(12) United States Patent
Witney

(10) Patent No.: US 9,366,153 B2
(45) Date of Patent: Jun. 14, 2016

(54) METHOD AND SYSTEM FOR STEAM PURITY MONITORING THROUGH USE OF HIGH ELECTRON MOBILITY TRANSISTORS

(71) Applicant: GENERAL ELECTRIC COMPANY, Schenectady, NY (US)

(72) Inventor: Andrew Batton Witney, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 867 days.

(21) Appl. No.: 13/689,808

(22) Filed: Nov. 30, 2012

(65) Prior Publication Data

US 2014/0154047 A1 Jun. 5, 2014

(51) Int. Cl.
*F01D 21/14* (2006.01)
*F01D 21/00* (2006.01)
*G01N 33/18* (2006.01)

(52) U.S. Cl.
CPC .............. *F01D 21/003* (2013.01); *F01D 21/14* (2013.01); *G01N 33/182* (2013.01)

(58) Field of Classification Search
CPC ................................ F01D 21/14; F01D 21/003
See application file for complete search history.

(56) References Cited

U.S. PATENT DOCUMENTS

| 4,455,530 A | 6/1984 | Lee et al. |
| 5,353,628 A | 10/1994 | Bellows |
| 2011/0084713 A1 | 4/2011 | Ren et al. |

FOREIGN PATENT DOCUMENTS

JP 06093808 A * 4/1994

OTHER PUBLICATIONS

JP 06093808 A Machine Translation. Accessed JPO website on Dec. 7, 2015. 3 pages.*

* cited by examiner

*Primary Examiner* — Richard Edgar
(74) *Attorney, Agent, or Firm* — McNees Wallace & Nurick LLC

(57) ABSTRACT

A method or system for steam purity monitoring in a steam powered turbine includes providing a chloride-sensing device in a steam flow path; generating a signal from the chloride-sensing device indicative of a concentration level of chloride ions in a steam flow; and indicating a concentration level of chloride ions in a steam flow. The steam turbine includes a rotor, a rotating shaft and a plurality of axially spaced rotor wheels. A plurality of rotating blades is mechanically coupled to each rotor wheel. A chloride-sensing device is disposed in a steam flow path. A controller is arranged to generate a signal from the chloride-sensing device indicative of a concentration level of chloride ions in a steam flow and indicate a concentration level of chloride ions in a steam flow.

15 Claims, 2 Drawing Sheets

METHOD AND SYSTEM FOR STEAM PURITY MONITORING THROUGH USE OF HIGH ELECTRON MOBILITY TRANSISTORS

FIELD OF THE INVENTION

The application generally relates to a method of monitoring the purity of steam. The application relates more specifically to monitoring the presence of chloride ions in steam to notify the operator of an emergency condition.

BACKGROUND OF THE INVENTION

Chloride detection technology by conventional detectors cannot sense low chloride levels that are corrosive when present in a steam turbine. As a result, real-time monitoring for chloride is only possible by proxy methods, for example, monitoring of sodium levels, or measurement of cation conductivity. Proxy methods such as cation conductivity do not focus specifically on chloride, which is among the primary corrosive elements present in steam chemistry.

Ion chromatography is another method used for detection of chloride in real time. However, ion chromatography is a complex and expensive method that requires skilled operators and preparation of reagents.

Carefully designed transistors have been shown capable of detecting chloride ions at the sub-parts-per-billion level in real time. Such detection capability is of great interest to steam turbine owners, as severe corrosion may be caused to a turbine from the presence of even very low levels of chloride.

This present invention proposes a method of applying chloride detection technology in a chloride detection system for steam turbines. Chloride detection using chloride-sensitive transistors is solid-state, and does not require ion-selective membranes or reagents to detect the presence of chloride.

Intended advantages of the disclosed systems and/or methods satisfy one or more of these needs or provide other advantageous features. Other features and advantages will be made apparent from the present specification. The teachings disclosed extend to those embodiments that fall within the scope of the claims, regardless of whether they accomplish one or more of the aforementioned needs.

BRIEF DESCRIPTION OF THE INVENTION

One embodiment relates to a method for steam purity monitoring. The method includes providing a chloride-sensing device in a steam flow path; generating a signal from the chloride-sensing device indicative of a concentration level of chloride ions in a steam flow; and indicating a concentration level of chloride ions in a steam flow.

Another embodiment relates to a system for steam purity monitoring. The system includes a steam turbine. The steam turbine includes a rotor, a rotating shaft and a plurality of axially spaced rotor wheels. A plurality of rotating blades is mechanically coupled to each rotor wheel. The blades are arranged in rows extending circumferentially around each rotor wheel. A plurality of stationary nozzles extends circumferentially around the shaft. Nozzles are axially positioned between adjacent rows of the blades. The nozzles cooperate with the blades to form a stage and define a portion of a steam flow path through the turbine. A chloride-sensing device is disposed in a steam flow path. A controller is arranged to generate a signal from the chloride-sensing device indicative of a concentration level of chloride ions in a steam flow and indicate a concentration level of chloride ions in a steam flow.

Still another embodiment relates to a method for steam purity monitoring. The method includes providing an ion-sensing device in a steam flow path; generating a signal from the ion-sensing device indicative of a concentration level of ions in a steam flow; and indicating a concentration level of ions in a steam flow; wherein the ion is selected from one of sulfate, fluoride, acetate, formate, and chloride; and wherein the ion-sensing device is tuned for the selected ion.

Certain advantages of the embodiments described herein are reliable detection of chloride at low-to-sub parts-per-billion level allowing turbine operators to detect and remedy dangerous condenser leaks before chloride levels increase to levels that may seriously damage the turbine.

A steam turbine with the capability to monitor its chloride content directly, integrated with the controller, may be able to eliminate most chemistry-related interruptions in power generation.

Alternative exemplary embodiments relate to other features and combinations of features as may be generally recited in the claims.

DETAILED DESCRIPTION OF THE INVENTION

Figure 1:
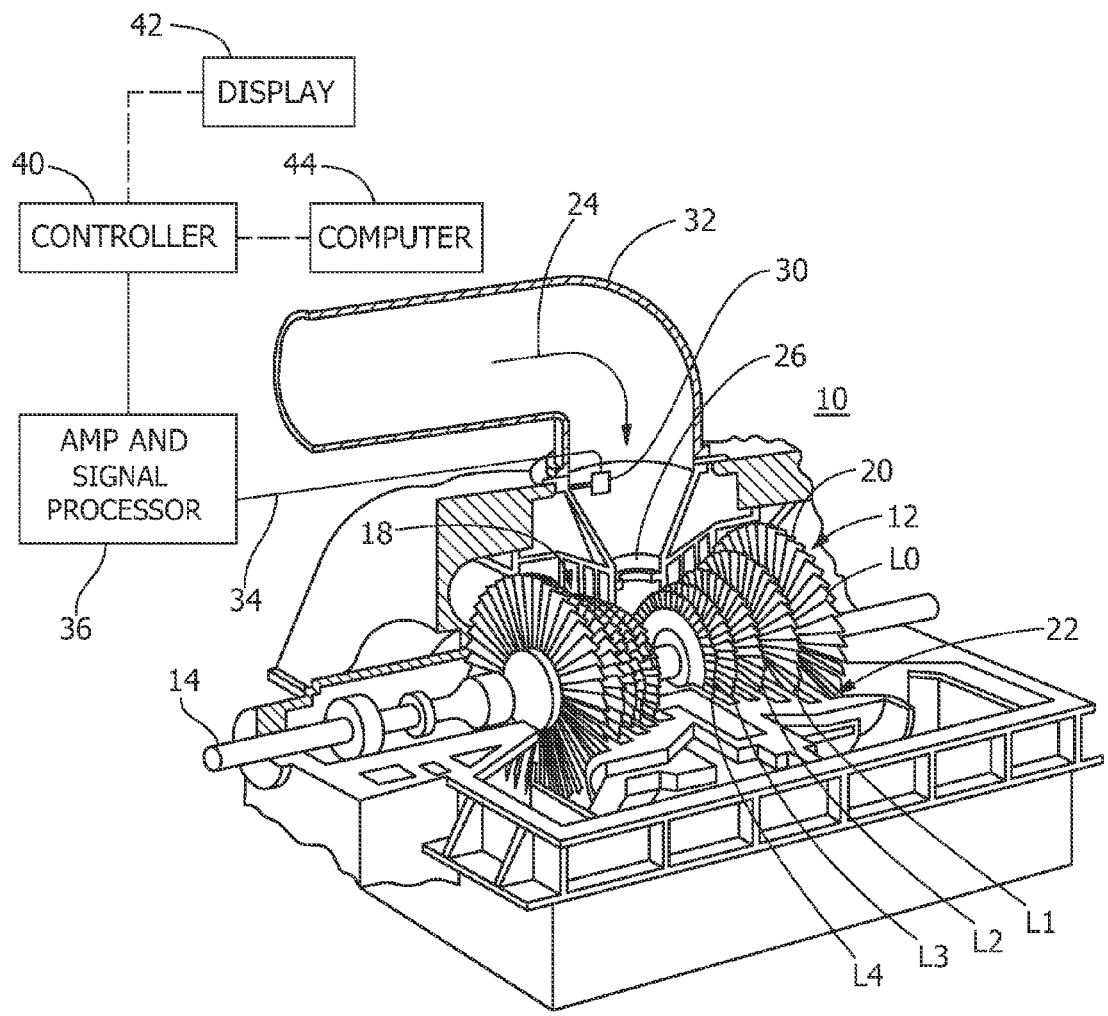
FIG. 1 is an exemplary steam turbine with a chloride sensing device.

In one embodiment as illustrated by FIG. 1, a turbine 10 may be a condensing steam turbine or a non-condensing steam turbine. Turbine 10 includes a rotor 12, a rotating shaft 14 and a plurality of axially spaced rotor wheels 18. A plurality of rotating blades or "buckets" 20 are mechanically coupled to each rotor wheel 18. Blades 20 may be arranged in rows that extend circumferentially around each rotor wheel 18. A plurality of stationary nozzles 22 extends circumferentially around shaft 14. The nozzles may be axially positioned between adjacent rows of blades 20. Stationary nozzles 22 cooperate with blades 20 to form a stage and to define a portion of a steam or hot gas flow path through turbine 10.

Gas or steam 24 enters an inlet 26 of turbine 10 and is channeled through stationary nozzles 22. Nozzles 22 direct gas or steam 24 downstream against blades 20. Gas or steam 24 passes through the remaining stages imparting a force on blades 20 causing shaft 14 to rotate. At least one end of turbine 10 may extend axially away from rotor 12 and may be attached to a load or machinery (not shown) such as, but not limited to, a generator, and/or another turbine.

Turbine 10 may have multiple stages. In one embodiment, turbine 10 may include five stages. The five stages are referred to as L0, L1, L2, L3 and L4. Stage L4 is the first stage and is the smallest (in a radial direction) of the five stages. Stage L3 is the second stage and is the next stage in an axial direction. Stage L2 is the third stage and is shown in the middle of the five stages. Stage L1 is the fourth and next-to-last stage. Stage L0 is the last stage and is the largest stage in the radial direction. It is to be understood that five stages are shown as one example only, and each turbine may have more or less than five stages. Also, as will be described herein, the teachings of the invention do not require a multiple stage turbine.

As shown in FIG. 1, a chloride-sensing device 30 is placed within the inlet 26 or adjacent to inlet 26, e.g., within a steam inlet conduit 32. Chloride-sensing device 30 measures chloride ion concentration of the steam flowing in inlet conduit 32.

Chloride-sensing device 30 is connected in electrical communication via signal wires 34 with a signal amplifier 36. Signal amplifier 36 receives a signal from chloride-sensing device 30 indicative of a concentration level of chloride ions in the steam. Signal amplifier 36 may include additional signal processing circuitry for conditioning the signal from chloride-sensing device 30. Signal amplifier 36 provides a voltage gain and power increase to the signal so that the signal is acceptable for input to a controller 40. Controller 40 receives the amplified signal and determines based on the amplified signal whether the chloride ion level present in the steam is above or below a predetermined threshold. If above the threshold, controller 40 may generate an alarm or message, e.g., to an operator display 42 or a computer 44 controlling the operation of turbine 10, so that appropriate action may be taken. In one embodiment a plurality of predetermined threshold levels may be used to indicate an increasing chloride ion concentration over a range of chloride ion concentration levels to alert the turbine operator before chloride ion concentration levels reach an unacceptable level.

Controller 40 may be configured to initiate remedial action while operation of the turbine continues, e.g., in the case of an extreme upset, automatic dosing of the system with phosphate would mitigate chloride; an alarm indicating to the operator to reduce steam pressure (or automatic reduction of pressure) may also be appropriate responses; to shut down the turbine to prevent further exposure to the chloride ions; to display or generate warnings to operators that potentially damaging levels of chloride ion concentration are present or anticipated in the steam. In addition or in the alternative, controller may retain historical records of chloride ion concentrations for subsequent retrieval and analysis.

Chloride-sensitive transistors, e.g., as high electron mobility transistors (HEMTs), may be used in the chloride sensing device 30. Chloride-sensitive transistors may be packaged or designed to be suitable for the turbine environment, e.g., temperatures, pressures and corrosive elements present in the steam path.

Figure 2:
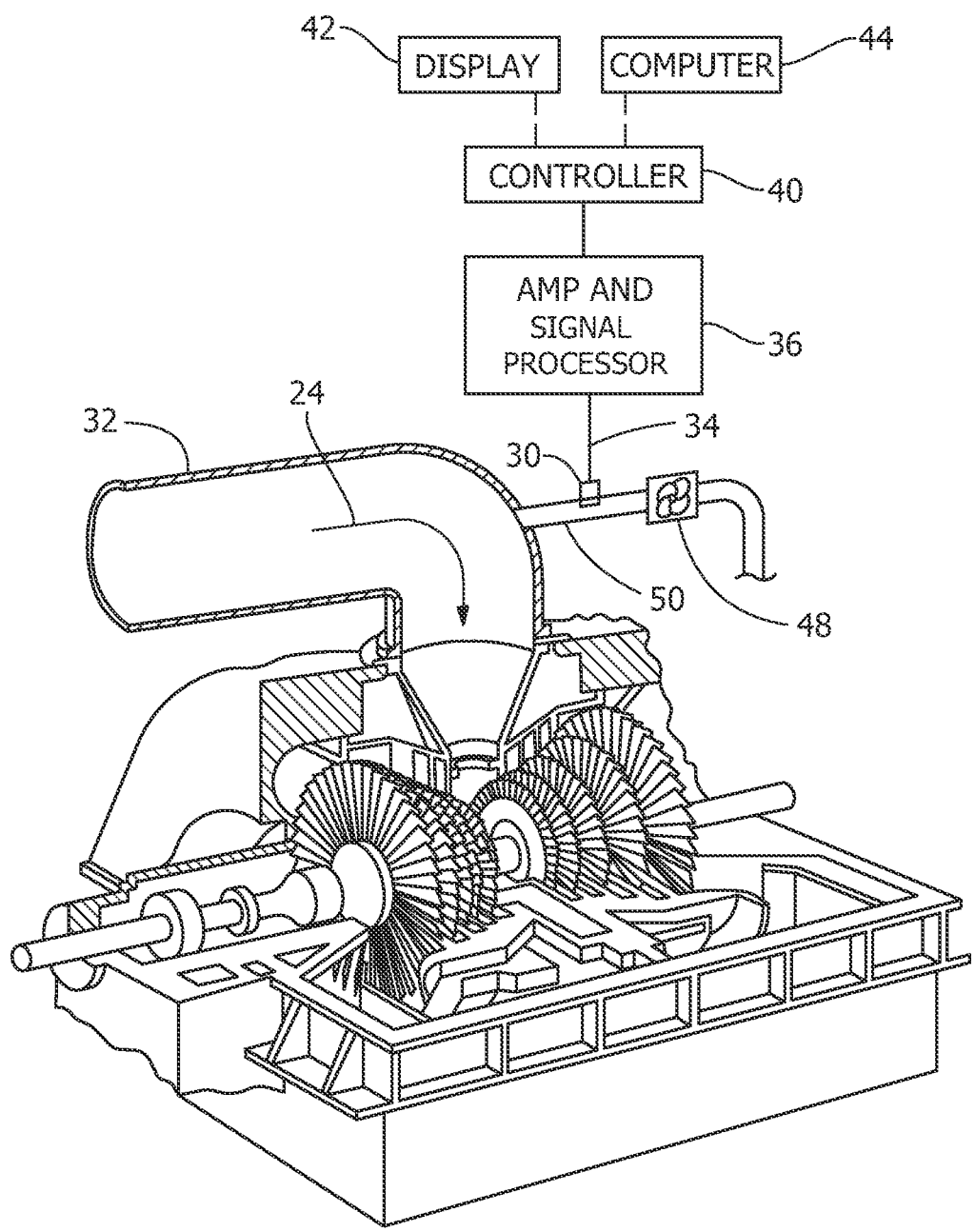
FIG. 2 is an alternate embodiment of the steam turbine with chloride sensing device.

Referring to FIG. 2, another embodiment is illustrated in which steam may be extracted from a suitable location along the steam path, and the chloride detected by the chloride-sensitive transistor at a location outside the turbine. A steam sampling pipe 50, e.g., an isokinetic sampling nozzle or probe, is connected in fluid communication with steam inlet conduit 32. A fan 48 or similar device may optionally be used to draw steam into steam sampling pipe 50. Chloride sensing device 30 is disposed within steam sampling pipe 50 and detects a level of chloride ion concentration. The output signal from chloride sensing device 30 is then processed in the same manner as described above with respect to FIG. 1.

In another embodiment the method may be used to detect other ions of interest to a steam turbine: sulfate, fluoride, acetate, formate, and others, for steam purity monitoring, e.g., by tuning the sensors to respond to the presence of such other chemicals.

The present application contemplates methods, systems and program products on any machine-readable media for accomplishing its operations. The embodiments of the present application may be implemented using an existing computer processors, or by a special purpose computer processor for an appropriate system, incorporated for this or another purpose or by a hardwired system.

It is important to note that the construction and arrangement of the chloride sensing system and method for monitoring steam purity, as shown in the various exemplary embodiments is illustrative only. Although only a few embodiments have been described in detail in this disclosure, those who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

As noted above, embodiments within the scope of the present application include program products comprising machine-readable media for carrying or having machine-executable instructions or data structures stored thereon. This also includes any web applications which may be delivered from a web site and run within a web browser such as Adobe Flash® or Microsoft Silverlight®. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

It should be noted that although the figures herein may show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the application. Likewise, software implementations could be accomplished with standard programming techniques with rule based logic and other logic to accomplish the various connection steps, processing steps, comparison steps and decision steps.

It should be understood that the application is not limited to the details or methodology set forth in the following description or illustrated in the figures. It should also be understood that the phraseology and terminology employed herein is for the purpose of description only and should not be regarded as limiting.

While the exemplary embodiments illustrated in the figures and described herein are presently preferred, it should be understood that these embodiments are offered by way of example only. Accordingly, the present application is not limited to a particular embodiment, but extends to various modifications that nevertheless fall within the scope of the appended claims. The order or sequence of any processes or method steps may be varied or re-sequenced according to alternative embodiments.

The invention claimed is:

1. A method for steam purity monitoring comprising:
   providing a chloride-sensing device in a steam flow path, the chloride-sensing device comprises a chloride-sensitive transistor;
   generating a signal from the chloride-sensing device indicative of a concentration level of ions in a steam flow; and
   indicating a concentration level of chloride ions in a steam flow.

2. The method of claim 1, further comprising measuring chloride ion concentration of the steam flowing in an inlet conduit.

3. The method of claim 1, further comprising amplifying the signal from the chloride-sensing device.

4. The method of claim 3, further comprising conditioning the signal with signal processing circuitry and inputting the signal after processing to a controller.

5. The method of claim 3, wherein the step of amplifying comprises providing a voltage gain and a power increase to the signal so that the signal is acceptable for input to a controller.

6. The method of claim 1,
   further comprising determining based on the signal whether a chloride ion level present in the steam is above or below a predetermined threshold; and
   further comprising generating an alarm or message in response to detecting a chloride ion level greater than the predetermined threshold.

7. The method of claim 6, wherein the step of generating further comprises communicating the alarm to an operator display or a computer controlling the operation of a steam turbine.

8. The method of claim 1,
   further comprising determining based on the signal whether a chloride ion level present in the steam is above or below a predetermined threshold; and
   further comprising initiating remedial action in response to the signal being equal to or exceeding the predetermined threshold while operating a steam turbine.

9. The method of claim 1, further comprising packaging the chloride-sensitive transistors suitable for a steam turbine environment.

10. A system for steam purity monitoring, comprising:
    a chloride-sensing device disposed in a steam flow path, the chloride-sensing device comprises a chloride-sensitive transistor;
    and a controller configured to generate a signal from the chloride-sensing device indicative of a concentration level of chloride ions in a steam flow and to indicate a concentration level of chloride ions in a steam flow.

11. The system of claim 10, further comprising a signal amplifier disposed in a path between the chloride-sensing device and the controller, the amplifier configured to receive the signal and provide a voltage gain and power increase to the signal for input to the controller.

12. The system of claim 11, further comprising signal processing circuitry associated with the amplifier, the signal processing circuitry configured to condition the signal from chloride-sensing device for input to the controller.

13. The system of claim 12,
    wherein the controller is configured to receive the signal and determine based on the signal whether the chloride ion level present in the steam is above or below a predetermined threshold; and
    wherein the controller is further configured to generate an alarm or message in response to the signal indicating a chloride ion level above the predetermined threshold.

14. The system of claim 10, wherein the system further comprises a steam turbine comprising a rotor, a rotating shaft and a plurality of axially spaced rotor wheels; a plurality of rotating blades coupled to each rotor wheel, a plurality of stationary nozzles cooperative with the blades to form a stage, the nozzles defining a portion of the steam flow path through the turbine.

15. A method for steam purity monitoring comprising:
    providing an ion-sensing device in a steam flow path, the ion-sensing device comprising a chloride-sensing transistor;
    generating a signal from the ion-sensing device indicative of a concentration level of ions in a steam flow; and
    indicating a concentration level of ions in a steam flow;
    wherein the ion is selected from one of the following: sulfate, fluoride, acetate, formate, and chloride; and
    wherein the ion-sensing device is tuned for the selected ion.

* * * * *